United States Patent [19]

Onopchenko et al.

[11] 4,215,226

[45] Jul. 29, 1980

[54] SELECTIVE HYDROGENATION OF NITROAROMATIC ACETYLENES OVER AN UNSUPPORTED RUS$_2$ CATALYST

[75] Inventors: Anatoli Onopchenko, Monroeville; Edward T. Sabourin, Allison Park; Charles M. Selwitz, Monroeville, all of Pa.

[73] Assignee: Gulf Research & Development Company, Pittsburgh, Pa.

[21] Appl. No.: 958,163

[22] Filed: Nov. 6, 1978

[51] Int. Cl.$^2$ .................... C07C 79/22; C07C 85/11; C07C 85/24

[52] U.S. Cl. .................... 568/705; 260/571; 260/575; 260/580; 260/578

[58] Field of Search ............ 568/704, 705; 260/571, 260/470 P, 575, 578, 580, 575, 474 A

[56] References Cited

U.S. PATENT DOCUMENTS 3,845,018  10/1974  Bilow et al. .................... 568/705

FOREIGN PATENT DOCUMENTS 1431640  4/1976  United Kingdom .................... 568/705

*Primary Examiner*—Werren B. Lone

[57] ABSTRACT

Aromatic nitroacetylene compounds wherein both the nitro and acetylene groups are directly connected to aromatic ring carbon atoms are hydrogenated in dilute concentration in an inert solvent at high conversion levels to selectively reduce the nitro function using an unsupported ruthenium disulfide catalyst. Of particular interest is the preparation of an aminophenylacetylene from a nitrophenylacetylene.

12 Claims, No Drawings

SELECTIVE HYDROGENATION OF NITROAROMATIC ACETYLENES OVER AN UNSUPPORTED RUS₂ CATALYST

This invention relates to a process for the selective hydrogenation of nitro groups on a nitroaromatic acetylene compound and in particular to the preparation of an aminophenylacetlyene from a nitrophenylacetylene over an unsupported ruthenium disulfide catalyst.

BACKGROUND OF THE INVENTION

The recent introduction of acetylene-terminated polyimides to produce cured reaction products which are stable at very high temperatures of 450° C. and up has created an interest and need to produce the polyimides at attractive and competitive costs. The prime difficulty in the preparation of the acetylene-terminated polimides which are described, for example, in U.S. Pat. No. 3,845,018 and U.S. Pat. No. 3,879,349, both to Norman Bilow et al, is the preparation of the monomers which include in one instance the preparation of meta-aminophenylacetylene (APA). This invention relates to the discovery of an unsupported ruthenium disulfide catalyst which selectively converts at high conversion levels the nitroaromatic acetylene compounds used in the process of this invention, e.g., nitrophenylacetylene, to the desired APA, provided the charge stock nitroaromatic acetylene is contacted with the catalyst in a dilute concentration in an inert solvent. By a "dilute concentration" is meant a concentration of less than about six weight percent. By following the teachings of this invention, high conversions of over 50 weight percent of the nitroaromatic acetylene are achieved, together with very high selectively of well over 70%, typically well over 90%.

DESCRIPTION OF THE PRIOR ART

The description of the preparation of APA contained in the teachings of Bilow et al in U.S. Pat. No. 3,845,018 involves a large number of expensive and time-consuming steps. Thus Bilow et al in Column 4, lines 41 et seq., teach that an aromatic compound having both nitro and acetylene substituents is reacted, preferably under reflux, with dimethylformamide and phosphorus oxychloride to convert the acetyl radical to —C(Cl)═CHCHO. The reaction is exothermic, and external cooling is needed to keep it at approximately room temperature. The B-chloro-substituted aldehyde radical is converted to —C≡CH by refluxing a solution of the compound in p-dioxane and sodium hydroxide. The product is extracted with an organic solvent such as diethylether; the organic solution is dried; the solvent is removed; and the product recovered by vacuum distillation.

Improved techniques over those taught by Bilow et al obviously have to be developed in order to improve the competitve position of the resultant acetylene-terminated polyimides in the marketplace.

One desirable technique to prepare aminophenylacetylene is to first prepare nitrophenylacetylene and then selectively hydrogenate the nitro group. This is a considerably difficult problem, since both the nitro and acetylene groups directly connected to an aromatic ring carbon atom are two of the most reactive groups known for hydrogenation Undoubtedly the difficulty of selectively hydrogenating a nitro group in the conjoint presence of an acetylene moiety directly attached to an aromatic ring carbon atoms accounts for the literature referring to the use of chemical reduing agents for the reduction of nitro groups. For example, the literature refers to the use of ozone in ammonium hydroxide (A. Burawoy and J. T. Critchley, *Tetrahedron, No.* 5, 340 (1959); sodium hydrosulfite (see *Organic Syntheses, Coll. Vol. III*, John Wiley & Sons, Inc., New York, NY 1966 p. 69); ammonium sulfite (E. H. Huntress, L. N. Stanley and A. S. Parker, *J. Am. Chem. Soc.*, 56 241 (1934)); ferrous sulfate (U.S. Pat. No. 3,845,018 (1974)); stannous chloride (H. M. Woodburn and C. F. Stuntz, *J. Am. Chem. Soc.*, 72, 1361 (1950); and thiourea dioxide (K. Nakagawa and K. Minami, *Tetrahedron Lett.*, No. 5, 343 (1972)) for the chemical reduction of nitro groups. The procedures, however, in the referred-to literature are generally tedious and unattractive for commercial application. Catalytic hydrogenation with molecular hydrogen is preferable for reasons of economy, safety and flexibility. No satisfactory catalytic method for the selective hydrogenation of aromatic nitro compounds in the conjoint presence of an acetylenic moiety where the acetylenic carbon is directly connected to an aromatic ring carbon atom has been reported as yet. Sokol'skii, *Dokl. Vses. Konf. Khim. Atsetilena*, 4th, 1973, 3, 325; *Chem. Abs.*, 79, 77771r (1973)). Reduction of phenylacetylene over palladium on alumina occurs two to three times faster in the presence of nitrobenzene than in its absence. (K. A. Zhubanov, B. V. Sokol'skii, E. P. Mazin, et al., *Zh. Prikl. Khim.*, 47, (8) 1885 (1974); *Chem. Abs.*, 81, 151684z (1974)). Hennion and Barrett hydrogenated propargyl esters of p-nitrobenzoic acid over palladium on barium sulfate and converted the ethynyl group to vinyl without affecting the nitro functionality (G. F. Hennion and S. O. Barret, *J. Am. Chem. Soc.*, 79, 2146 (1957). Grob and Jenny in U.S. Pat. No. 3,118,946, hydrogenated 2-nitrooctadec-4-yn-1,3-diol over Lindlar catalyst and obtained 2-nitrooctadec-4-en-1,3-diol selectively. It is obvious that the selective hydrogenation of a nitro group in the conjoint presence of the highly reactive acetylenic function where both are directly connected to aromatic ring carbon atoms on the same molecule presents a formidable problem. It is apparent that a wide spectrum of products could be expected since the nitro funtion, the aromatic ring and the acetylene function can all be partially or completely hydrogenated.

The most pertinent prior art to the subject invention is believed to be the more recent British Pat. No. 1,431,640, published Apr. 14, 1976, and entitled, "Process for the Preparation of Aliphatically Unsaturated Aromatic Amino Compounds".

The British patent is mainly concerned with the catalytic hydrogenaton of 4,4'-dinitrostilbene-2,2' disulfonic acid to the corresponding 4,4'-diamino-2,2' disulfonic acid, as half of their working examples are with this substrate Exs. 4–6 and 15–23). The British patent does have general teachings to the effect that aromatic nitro compounds wherein the nitro group is aromatically bonded and which contain aliphatic C—C multiple bonds can be selectively catalytically reduced so that the nitro group is converted to the amino group without substantial loss of the C—C multiple bonds. All of the working examples, save one, are concerned with the selective reduction of aromatically bonded nitro groups in the presence of carbon to carbon double bonds. The one exception is the selective hydrogenation of 2-acetylamino-4-nitrobenzoic acid propargyl ester (ex. 12) to produce the corresponding aminobenzoic acid propargyl ester. The propargyl ester function, of course, contains an acetylenic group, but it is noted that this acetylenic group is not directly bonded to an aromatic carbon atom and thus is not "activated" by the ring.

Thus the British patent does not have a working example utilizing a charge stock which contains both a nitro group and an acetylenic group directly attached to aromatic ring carbon atoms. Furthermore, the list of suitable examples of aromatic nitro compounds contained on page 3 of the British patent cites no aromatic compound wherein both the nitro and acetylenic linkages are directly connected to aromatic carbon atoms. The British teachings to effect the above described selective reduction involve hydrogenation in the presence of a metal sulfide of the formulat $MS_x$, wherein x is a number from 1 to 4, and M represents a metal atom of Group VIII of the Periodic System of the elements, or represents rhenium. According to the British patent, the reaction can occur at temperatures from 20° to 140° C. and at pressures of 5 to 150 bars of hydrogen pressure. The catalyst may be utilized unsupported (p. 2, Col. 2), or the metal sulfides may be deposited on a support wherein the active metal sulfide on the support can be between 0.1 to 5 percent by weight (p. 3, Col. 1). The patent also teaches that the catalytically active component can be employed in amounts of 0.005 to 10 percent, especially 0.05 to 5 percent relative to the nitro compounds (p. 3, Col. 1, lines 8—11). The working examples use many different types of metal sulfide catalysts, including iron, cobalt, nickel, rhenium, platinum, and ruthenium, both supported and unsupported. (The more recently issued U.S. Pat. No. 4,051,177, dated Sept. 27, 1977, is based on part of the specification of the British patent but is limited in its teachings to the use of a cobalt sulfide catalyst).

Morris Freifelder in "Practical Catalytic Hydrogenation", Wily-Interscience Publishers, New York, NY (1971) on page 168 states that the nitro group attached to a benzene ring, with the exception of the acetylenic linkage, is the most amenable of all reducible systems to catalytic hydrogenation. According to the author, not enough work has been carried out on the reducibility of the triple bonds in the aromatic nitro group to state authoritatively that one will be selectively hydrogenated in the presence of the other. In most other instances, an aromatically bound nitro group will be peferentially reduced in the presence of another reducible function. On page 192 of the same reference, the author concludes that the nitro group is generally preferentially reduced in the presence of olefinic bonds.

A fair summary of the above teachings of the prior art would appear to suggest that the aromatic nitro group wherein the nitro group is directly attached to an aromatic carbon atom is a highly reducible group and that it will selectively hydrogenate in the presence of olefinic double bonds, and that such a nitro group will also selectively reduce in the presence of aliphatic carbon to carbon triple bonds which are present on a chain wherein the triple bond is not directly connected to an aromatic carbon atoms. Freifelder suggests that the selectively to the reduction of the nitro group in the conjoint presence of carbon to carbon triple bonds, both directly connected to the same aromatic nucleus, is not settled, and the recent British patent would appear to suggest a wide variety of metal sulfides to selectively reduce aromatic nitro groups on certain types of compounds containing, in addition, C-C multiple bonds.

In accordance with the invention, it has now been found that of the many supported and unsupported metal sulfide catalyst suggested by the prior art, a catalyst consisting essentially of unsupported ruthenium disulfide is surprisingly unique under certain conditions in the selective reduction of nitro groups in an aromatic nitro compound containing in addition an acetylene group directly connected to an aromatic ring carbon atom, even at high conversion levels of over 50%. The reaction in accordance with the invention proceeds by contacting a charge stock comprising an inert solvent and an aromatic nitro compound containing (i) at least one nitro group directly connected to an aromatic ring carbon atom and (ii) at least one acetylenic group having at least two carbon atoms and wherein at least one of the acetylenic groups is directly connected to an aromatic ring carbon atom with an unsupported catalyst containing essentially of ruthenium disulfide and in the added presence of free molecular hydrogen under reaction conditions such that (a) the charge stock is maintained substantially in the liquid phase;

(b) the weight percent of the aromatic nitroacetylene in the inert solvent is from one to about six weight percent;

(c) the reaction temperature is from 60° C. to 140° C.; and (d) the conversion of said nitro aromatic compound is greater than 50 weight percent.

DEFINITION OF THE CHARGE STOCK

The charge stock for the process of this invention is a nitro aromatic acetylene containing at least one nitro group directly connected to an aromatic ring carbon atom and at least one acetylenic group directly connected to an aromatic ring carbon atom through one of the acetylenic group carbon atoms. More preferably, the nitro aromatic compound charge stock has (i) from one to two nitro groups, (ii) from one to two acetylene moieties directly attached through an acetylene carbon atom to aromatic ring cargon atoms, and (iii) from one to two aromatic rings. The aromatic nucleus can be derived from benzene, naphthalene, bibenzyl, diphenyl, diphenyl oxide, diphenyl sulfide, or benzophenone, with the nitro and the acetylene groups being attached to the same or different aromatic rings. The nitro aromatic compound usually has from 8 to 16 carbon atoms and more usually has from 8 to 14 carbon atoms.

Most preferably the nitro aromatic acetylene charge stock utilized in the process of this invention has the formula:

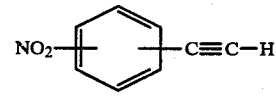

Suitable specific examples of charge stocks which fall within the scope of this invention include but are not limited to the following materials:
3-nitrophenylacetylene;
4-nitrophenylacetylene;
2-nitrophenylacetylene;
5-nitro-1-ethynylnaphthalene;
3-nitro-3'-ethynylbiphenyl;
4-nitro-4'-ethynylbenzophenone;
3-nitro-3'-ethynyl diphenyl ether; etc.

The nitro aromatic compound charge stocks described above can be prepared by any suitable procedure, and the method of preparation of these materials forms no part of the present invention. For example, nitrophenylacetylene itself can be prepared by the procedure of Bilow et al in U.S. Pat. No. 3,845,018.

The nitro aromatic charge stocks described above are selectively hydrogenated to produce the corresponding amino aromatic actylenes, and a list of specific examples would parallel this list of nitro aromatic compounds set forth above except "amino" would replace "nitro" in each compound.

In particular, this invention is concerned with the preparation of an aminophenylacetylene (especially metanitrophenylacetylene) acetylenes having the formula:

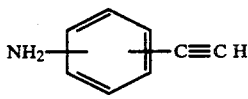

Specific examples of amino aromatic substituted acetylenes include:
o-,m- and p-aminophenylacetylene;
5-amino-1-ethynylnaphthalene;
3-amino-3'-ethynylbiphenyl;
4-amino-4'-ethynylbenzophenone;
3-amino-3'-ethynyl diphenyl ether; etc.

The desired product of the process of this invention is aminophenylacetylene which can, of course, be prepared directly from nitrophenylacetylene.

The aromatic nitroacetylenes described above are highly reactive as they contain both nitro and acetylene functions, both directly connected to an activating aromatic ring. It has been found necessary to operate the reaction in the presence of an inert solvent which functions not only as a heat control medium but also inhibits certain side reactions which tend to form sulfur-containing products by reaction of the triple bond in an aromatic nitro compound in some manner with the sulfur of the catalyst.

The type of solvent is not critical, but it is preferred to employ a solvent which is miscible with the water of reaction so that separate phases are not formed during the selective reduction reaction. This is especially important in batch phase operations using powdered catalysts which tend to clump in the presence of free water and thus prematurely stop the reaction. The amount of solvent to employ is critical to obtain high conversions and selectivities to the desired aminoaromatic acetylenes. It has been found that the concentration of the nitroaromatic acetylene in the inert solvent must be from about one weight percent to about six weight percent, preferably from about 2 to about 5 weight percent, and more preferably from about 2 to about 4 weight percent in order to obtain both high conversion and selectively to the production of the desired aminoaromatic acetylenes. It has been found that substantially complete conversion with selectivities of 70 to 100 percent to the desired aminoaromatic acetylenes can be achieved so long as the amounts of solvent are within the rather narrow ranges set forth above.

Examples of suitable solvents include but are not meant to be limited to: aliphatic alcohols having from 1 to 5 carbon atoms, such as methanol, ethanol, propanol, isopropanol and pentanol; organic esters having from 3 to 6 carbon atoms, such as ethyl acetate, methyl acetate; low molecular weight ethers, such as diethyl ether, tetrahydrofuran and p-dioxane; low molecular weight organic acids having from 2 to 5 carbon atoms, such as acetic acid, propionic acid; and toluene.

DESCRIPTION OF THE CATALYST

The catalyst which has been found unique for effecting the selective reduction reaction of this invention at high conversion levels of over 50 percent is an unsupported ruthenium disulfide.

The method of producing the catalytically active ruthenium disulfide is not critical, and any method described in the prior art is satisfactory. For example, a ruthenium sulfide from the reaction of ruthenium salts and hydrogen sulfide, or from the reaction of ruthenium and sulfur elements can be used. Some of the typical methods of catalyst preparation have been referred to in U.S. Patent 3,350,450 and references cited therein. As another example, see E. de Barry Barnet and C. L. Wilson's "Inorganic Chemistry", Longmar's Green & Co., London, England, 1953, p. 244, wherein a ruthenium salt or a ruthenate salt or treatment with aqueous sodium sulfide will give $RuS_2$. Other well known conventional methods include treatment of ruthenium salts with hydrogen sulfide.

As will be shown below, the active form of the unsupported ruthenium catalyst is $RuS_2$ where the Ru is in the +4 valence state. $RuS_2$ is converted during reaction to the RuS from where the Ru is in the +2 valence and reaction ceases. The conversion of Rus to Ru in the zero valent form was never observed under the mild reaction conditions of this invention. Thus the catalyst of this invention must contain at least some $RuS_2$ (ruthenium disulfide) in order to be active for promoting the selective hydrogenation reactions of this invention. Any means can suitably by employed to maintain the ruthenium in the $RuS_2$ state as reaction proceeds. Once such means would include the continuous or periodic addition of sodium sulfide to the reaction zone or sodium polysulfide, $H_2S$, etc.

In a preferred embodiment of the process, the ruthenium disulfide is produced by reacting a ruthenium salt such as ruthenium trichloride hydrate and an alkali or alkaline earth metal sulfide. Other suitable ruthenium salts which can be used include ruthenium nitrate, potassium ruthenate, sodium perruthenate, and ruthenium sulfate, and etc.

The weight ratio of the nitroaromatic acetylene to the ruthemium disulfide catalyst is not critical, but has an effect on the extent of hydrogenation. Suitably the weight ratio of the nitroaromatic acetylene to ruthenium as the metal is from 1:1 to 300:1 or higher, and usually the weight ratio is from 10:1 to 100:1. For maximum productivity and efficiency, one wishes to hydrogenate as much feed as possible per given amount of catalyst.

The selective reduction reactions of this invention can be operated using, for example, a batch of continuous process. In a batch process, the catalyst can be in any suitable form, but is usually in the form of a powder or a paste. The weight ratio of the nitroaromatic acetylene to the catalyst in the batch process is as defined above. In a continuous process, catalyst can be added separately or in admixture with the canrge stock continuously to one end of a stirred reactor while product and catalyst are continuously removed from the other end or points in between. The free molecular hydrogen necessary for the reduction reaction can be passed concurrently with the charge stock or can enter the reaction zone countercurrent to the charge stock. The hydrogen can be pure 100% hydrogen, but it is possible to use refinery hydrogen wherein the hydrogen content is between 70 and 95 volume percent.

The reaction conditions are mild and include a temperature from about 60° to 140° C., preferably 75° to 135° C. and more preferably from 85° to 125° C. The reaction rate below 60° C. is too low to be of commercial significance, while temperatures above about 140° C. tend to promote undesired reactions such as hydration, polymerization, and hydrogenation of acetylene groups.

The reaction pressure is not critical, and suitable reaction pressures include atmospheric to 150 atmospheres, preferably 10 atmospheres to 100 atmospheres. The reaction is operated, of course, in the presence of free molecular hydrogen, which at atmospheric pressure can be bubbled through the reaction mixture. The reaction is preferably operated at elevated hydrogen partial pressures of from 10 to 100 atmospheres (1.01 to 10.1 Mpa). The reaction time is likewise not critical and is a function of many variables including the type of charge stock and the reaction conditions. Usually the reaction times are from 10 minutes to 100 hours; more usually the reaction time is from 30 minutes to 10 hours.

It has been found that the nitro group on the substituted nitroaromatic acetylene charge stocks of this invention is selectively reduced at high conversion levels to give unexpectedly high yields of the desired substituted amino aromatic acetylenes. The process of this invention can be operated within the range of conditions set forth above to provide weight percent conversions of the nitroaromatic compound chanrge stocks of over 50 weight percent and usually 70 to 100 percent, although, obviously, lower conversion can occur. The selectivities to the production of the desired corresponding amino aromatics still containing the acetylene group are usually over 70 percent and can be from 90 to 100 percent, even at the higher conversion levels.

The product recovery is not difficult and can suitable be achieved by simple vacuum or steam distillation to separate the product from unreacted charge stock. Obviously care must be taken in the distillation of the products (or other recovery technique) from the realization that the products contain an acetylene function which may lead to polymerization giving off considerable amount of heat.

The invention will be further described with reference to the following experimental work.

EXPERIMENTAL WORK

In all of the working Examples, the nitroaromatic acetylene charge stock was m-nitrophenylacetylene. Unless otherwise noted, a batch-type reaction was employed, as follows:

(1) The feed stock was dissolved in isopropanol or methanol, which were used as the solvents;

(2) the catalyst was added, and the mixture placed into a standard 500 ml Parr hydrogenation bottle, or a 1-liter autoclave;

(3) the system was purged with hydrogen;

(4) the desired operating temperature was adjusted, and then pressured with free molecular hydrogen to desired pressure from 50 psig (0.34 MPa) to about 1000 psig (6.9 MPa), and maintained in the stipulated pressure range by periodic injection of measured amounts of additional hydrogen.

(5) the reaction was allowed to proceed until the theoretical amount of hydrogen was consumed to convert the —$NO_2$ groups in the charge stock to —$MH_2$ and water as well as couled be determined. (The hydrogen consumed was measured either by pressure drop or by gas-liquid chromatography of aliquots.)

(6) After the reaction was deemed complete, the reaction mixture was allowed to cool to room temperature and the mixture was then filtered through a glass frit to remove the datalyst.

(7) The product was an amber colored liquid which was recovered by distillation.

In all of the working Examples in this specification, the term "conversion" shall mean the weight percent of the nitroaromatic acetylene, i.e. nitrophenylacetylene, converted to all products; and "selectively" shall mean the weight of aminoaromatic acetylene, i.e. aminophenylacetylene found by gas-liquid chromatography analysis in the reaction product divided by the weight of such amino aromatic acetylene theoretically expected. "Yield" is the numerical product of conversion times selectivity.

EXAMPLE 1

Preparation of Ruthenium Sulfide Catalyst

A first solution of 5.0 grams of ruthenium trichloride hydrate ($RuCl_3 \cdot XH_2O$, 40% Ru) was dissolved in 50 ml of distilled water, blanketed by nitrogen to prevent oxidation, and heated to 65° C. A second solution of 25 grams of sodium sulfide nonahydrate in 75 ml of distilled water was heated to about 50° C. and added, while stirring, to the first solution of ruthenium chloride over 15 minutes. Reaction was continued for 30 minutes, and the catalyst was filtered while hot through a medium porosity glass-cindered funnel. The catalyst was washed two times with 100 ml of boiling water each time and dried on the funnel under nitrogen for 30 minutes. A total of 13.0 grams of black, paste-like ruthenium sulfide was obtained, containing about 25% of solids. Analysis of catalyst by X-ray photoelectron Spectorscopy (XPS) indicated ruthenium to be in the +4 valency state, corresponding to $RuS_2$ structure.

EXAMPLE 2

Five grams of 3-nitrophenylacetylene in 197 grams of isopropanol (ca. 2.5% conc.) was hydrogenated in the presence of 1.5 grams of ruthenium sulfide catalyst (Ex. 1), following the course of reaction by a pressure drop. After 50 minutes of reaction at 110° C. and 1000 psig (6.9 MPa), reaction was stopped. Filtration of the reaction mixture to recover the catalyst, followed by evaporation is isopropanol, afforded 4.0 grams of oily product. Analysis by internal stadard method by gas chromatography indicated that each component in the product was visible on the chromatogram. Analysis showed that 87% of the feed had been converted, with a 94% selectivity to desired 3-aminophenylacetylene. The major byproduct was 3-aminostyrene. Table 1 below summarizes the results.

EXAMPLE 3

A total of 10 grams of 3-nitrophenylacetylene in 197 grams of isopropanol (ca 5% conc.) were hydrogenated. in the presence of 2.5 grams of ruthenium sulfide paste. After reaction of 93 minutes at 100° C. and a 1000 psig (6.9 MPa) of hydrogen, reaction was stopped. Analysis showed that only 85% of products were visible by chromatography. The remaining 15% must have been present as high boiling polymeric materials. Analysis of the visible portion of materials showed 99% conversion of feed and a 94% selectivity to 3-aminophenylacetylene. Analysis of spent catalyst by X-ray Photoelectron Spectroscopy (XPS) showed ruthenium to be in the +2 valency state, corresponding to RuS. Treatment of spent catalyst with sodium sulfide solution converted ruthenium to the active $RuS_2$ state. The results are summarized on Table 1 below.

EXAMPLE 4

In this experiment, 25 grams of 3-nitrophenylacetylene in isopropanol (11% conc.) was hydrogenated over 4.4 grams of ruthenium sulfide for 23 minutes at 110° C. and 1000 psig (6.9 MPa) of hydrogen pressure. Analysis of the product as in Example 2 showed that only 35% of product was visible by chromatography. Analysis of honey-like consistency product, visible by chromatography, indicated at 75% feed conversion and a 94% 3-aminophenylacetylene selectivity. The results are shown on Table 1 below.

The light boiling products were distilled off under reduced pressure (about 1.0 mm of mercury), and the residue was analyzed by nuclear magnetic resonance spectroscopy and infrared spectroscopy. The nuclear magnetic spectrum contained a sharp singlet peak at about 2.5 ppm, indicative of acetophenone structure, $ArCO\underline{C}H_3$, and a sharp singlet peak at about 2.2 ppm for $ArC(\underline{C}H_3)=NAr$ structure. Acetophenone structure was also supported by infrared band at 1670 cm$^{-1}$ (strong). As expected, the spectrum had very little of acetylene structures ($ArC\equiv C\underline{H}$) and also of aromatic amines. This data indicates that considerable hydration of phenylacetylene must have taken place, followed by condensation of acetophenone formed with amine to produce Schiff bases, and further polymerizations.

EXAMPLE 5

In this experiment, an even higher concentration of nitrophenylacetylene was used in Example 4, as well as the lower amount of catalyst. Results showed that 90% of total product consisted of polymeric materials. The results are shown on Table 1 below.

EXAMPLE 6

In this experiment, a large amount of feed per given amount of catalyst as Ru metal (300:1) was used. Reaction stopped after taking up hydrogen for 140 minutes. As expected, hydrogen uptake rate was very small. Analysis showed only 16% conversion of feed. The results are shown in Table 1 below. No attempt was made to determine the higher boiling products formed, if any.

The results of Examples 2 and 3 indicate that ruthenium sulfide is a highly selective catalyst for preferentially hydrogenating an aromatic nitro group in the presence of an aromatic acetylene on the same molecule when low concentrations of 3-nitrophenylacetylene are used (up to about 6%). Increasing nitrophenylacetylene concentrations to 11% as in Example 4, or higher as in Example 5, results in the predominant production of polymeric materials. These results suggest that ruthenium sulfide is both an excellent hydrogenation catalyst as well as a hydration catalyst for acetylenes, each reaction proceeding at its own rate. By using higher concentrations of nitrophenylacetylene, it appears that hydration rates with ruthenium sulfide catalyst are enhanced considerably over those of hydrogenation.

EXAMPLE 7

In this example, the hydration characteristics of ruthenium sulfide catalyst were tested with 3-aminophenylacetylene, and compared with the less reactive, non-activated, 4-aminobenzoic acid, propargyl ester. For this purpose, 5.0 grams each of the above two aminoacetylenes were contacted over 3.4 grams of ruthenium sulfide paste in the presence of 375 grams of isopropanol and 75 grams of water under nitrogen. Reaction was carried out at 120° C., 1000 psig (6.9 MPa) of pressure, for four hours. After cooling and depressurizing, the product was filtered, and evaporated to dryness in a rotary evaporator. Analysis of the residue by gas chromatograph benzophenone as internal standard showed that over 95% of 4-aminobenzoic acid, propargyl ester, had survived the hydration reaction, as compared to only 60% in the case of 3-aminophenlyacetylene. About 5.5% of 3-aminophenylacetylene was converted to 3-aminoacetophenone. This Example showed that acetylene portion of the highly activated 3-aminophenylacetylene is about 25 times more susceptible to hydration than the non-activated propargyl group in 4-aminobenzoic acid ester.

TABLE 1

HYDROGENATION OF 3-NITROPHENYLACETYLENE OVER $RuS_2$ CATALYST
(110° C. and 1000 psig (6.9 MPa) $H_2$)

| Ex. No. | Catalyst paste, wet grams | Solvent: Isopropanol (IsoPrOH) grams | NPA[a] grams (wt % conc) | % $RuS_2$ on NPA | Reaction Time, min. | Pressure drop psig | Ratio of NPA to Catalyst, g/g Ru | NPA Conv. % | Internal Standard, % glc visible components | % Molar Select. APA[e] AS[f] Misc. (visible by glc) | | |
|---|---|---|---|---|---|---|---|---|---|---|---|---|
| 2 | 1.5 | 197 | 5 (2.5) | 7.4 | 50 | 80 | 22:1 | 87 | 99 | 94 | 5 | 1 |
| 3[d] | 2.5 | 197 | 10 (4.8) | 6.2 | 93 | 100 | 26:1 | 99 | 85 | 94 | 5 | 1 |
| 4 | 4.4 | 197 | 25 (11) | 5.8 | 23 | 230 | 28.1 | 75 | 35[b] | 94 | 5 | 1 |
| 5 | 2.2 | 197 | 50 (20) | 1.1 | 230 | 535 | 150:1 | 100 | 10[b] | 95 | 4 | 1 |
| 6 | 1.1 | 197 | 50 (17) | 0.5 | 140 | 95 | 300:1 | 16[c] | not determined | 94 | 4 | 2 |

[a] 3-nitrophenylacetylene
[b] Honey-like consistency
[c] Reaction stopped prematurely. No further hydrogen uptake was evident. Too much substrate per given amt. of Ru
[d] 100° C.
[e] APA = 3-aminophenylacetylene
[f] AS = aminostyrene

EXAMPLE 8

Preparation of 0.75% ruthenium sulfide on alumina catalyst

In the run for this Example, 5 grams of sodium sulfide nonahydrate were dissolved in 50 ml of distilled water to form a first solution, and heated to 90° C. 7.5 Grams of powdered gamma-alumina (Filtrol 86) were then added to the first solution to form a slurry. While stirring, to this slurry was added a second solution, prepared by dissolving 0.14 grams of $RuCl_3.1-3H_2O$ in 20 grams of distilled water, over a period of 5 minutes. The catalyst was filtered while hot, and washed four times with about 10 ml portions of boiling water. The catalyst was dried on a filter for about 30 minutes under nitrogen, and then stored in a tightly sealed container under nitrogen.

EXAMPLE 9

3.0 Grams of 3-nitrophenylacetylene in 130 ml of isopropanol were hydrogenated at 50° C. and 50 psig (0.34 MPa) of hydrogen pressure over one-half the amount of catalyst prepared above in Example 8, corresponding to 28 milligrams of ruthenium metal. After one hour, reaction was stopped since no hydrogen uptake was evident.

EXAMPLE 10

Example 9 was repeated using 5.0 grams of 3-nitrophenylacethylene in 197 grams of ispropanol at 110° C. and 1000 psig (6.9 MPa) of hydrogen pressure. After reaction of only 15 minutes, no further hydrogen uptake was evident and reaction was discontinued. Analysis showed that only 10% feed conversion was obtained and a 95% selectivity to 3-aminophenylacetylene. No attempt was made to determine whether polymeric products were formed.

EXAMPLES 11-13

Three batches of ruthenium sulfide catalyst on charcoal support were prepared to correspond to 0.5%, 2.0% and 5% as ruthenium metal. In a typical experiment, 15 parts of sodium sulfide nonahydrate were dissolved in 85 parts of water, heated to 90° C.; and one part of sulfur was then added. Reaction was continued while stirring at this temperature until sulfur had dissolved, and the commerical high surface area charcoal, powder (Pittsburgh Carbon Co.) was added in an amount sufficient that whenever ruthenium chloride is added, desired ruthenium metal concentrations will be obtained. A second solution was prepared by dissolving 15 parts of ruthenium trichloride hydrate (40% Ru) in 85 parts of water and adding to the first solution containing charcoal over 5-10 minutes. After filtration, washing with boiling water, and drying in a rotary evaporator for several hours, three batches of catalyst were prepared: Example 11, 0.5% Ru; Example 12, 2.0% Ru; and Example 13, 5.0% Ru on charcoal support.

EXAMPLES 14-20

Examples 14-20 are summarized in Table 2, which Examples employ supported ruthenium sulfides on charcoal under a variety of conditions. The only runs which gave any reaction at all are those employing 2.0% and 5.0% Ru on charcoal catalyst at 100° C. and 1000 psig (6.9 MPa) of hydrogen pressure. Examples 19 and 20 show that only low substrate conversions were obtained. It is possible that supported catalysts lead to catalyst poisoning through too strong an absorption of the acetylene function and are therefore not suited for 3-nitrophenylacetylene hydrogenation.

EXAMPLES 21-22

These Examples involve the preparation of rhodium sulfide (Ex. 21) and rhenium sulfide (Ex. 22) from the corresponding metal chloride hydrates, following procedure of Example 1.

EXAMPLE 23

Hydrogenation of 3-nitrophenylacetylene over the rhodium sulfide of Example 21 (summarized in Table 3) afforded only 40% selectivity to desired 3-aminophenylacetylene and a 48% selectivity to 3-aminostyrene. It is possible that hydrogenation went too far, i.e. aminostyrene resulted from aminophenylacetylene. To check this out, Example 24 was performed.

EXAMPLE 24

This run was carried out under partial substrate conversion using the rhodium sulfide catalyst of Example 21. Results showed only 26% selectivity to 3-aminophenylacetylene and a 55% selectivity to 3-nitrostyrene. It is clear then that rhodium sulfide catalyst has no appreciable specificity. The results are summarized in Table 3.

EXAMPLE 25

In this Example, the rhenium sulfide catalyst of Example 22 was used for hydrogenation of 3-nitrophenylacetylene. Results showed that only partial substrate conversion was obtained before reaction stopped completely. It is estimated that essentially equivalent amount of catalyst paste will be needed to convert 10 grams of substrate, i.e. 7.3 grams of paste or 4.0 grams of rhenium catalyst as metal, for every 10 grams of feed. The results are shown in Table 3 below.

The results of Examples 23-25 therefore indicate rhodium sulfide and rhenium sulfide to be poor catalysts for 3-nitrophenylacetylene hydrogenation.

TABLE 2

| | HYDROGENATION OF 3-NITROPHENYLACETYLENE (NPA) (% Ru as metal) | | | | | | | | | | | |
|---|---|---|---|---|---|---|---|---|---|---|---|---|
| Ex. No. | Catalyst | mg, Ru | NPA, g. | Ratio NPA/Ru | Temp. °C. | Pressure psig $H_2$ | (MPa) | Time, min. | NPA, % conv. | % Selectivity APA[a] | AS[b] | NS[c] | Others |
| 14 | 0.5% $RuS_2$/C | 3.4 | 3.0 | 882 | 24 | 50 | (0.34) | 35 | 0 | No reaction | | | |
| 15 | 0.5% $RuS_2$/C | 3.4 | 3.0 | 882 | 50 | 60 | (0.41) | 60 | 0 | No reaction | | | |
| 16 | 0.5% $RuS_2$/C | 16.9 | 15 | 887 | 100 | 1000 | (6.89) | 36 | 0 | No reaction | | | |
| 17 | 5.0% $RuS_2$/C | 67.5 | 3.0 | 44 | 24 | 50 | (0.34) | 49 | 0 | No reaction | | | |
| 18 | 5.0% $RuS_2$/C | 67.5 | 3.0 | 44 | 50 | 50 | (0.34) | 45 | 0 | No reaction | | | |
| 19 | 5.0% $RuS_2$/C | 236 | 15 | 63.5 | 100 | 1000 | (6.89) | 4 | 23 | 86 | 8 | 5 | 1 |
| 20 | 2.0% $RuS_2$/C | 73.5 | 15 | 204 | 100 | 1000 | (6.89) | 39 | 14 | 100 (rxn stopped after initial $H_2$ uptake of | | | |

TABLE 2-continued

HYDROGENATION OF 3-NITROPHENYLACETYLENE (NPA)
(% Ru as metal)

| Ex. No. | Catalyst | NPA, mg, Ru | NPA, g. | Ratio NPA/Ru | Temp. °C. | Pressure psig H$_2$ (MPa) | Time, min. | NPA, % conv. | % Selectivity APA$^a$ | AS$^b$ | Ns$^c$ | Others |
|---|---|---|---|---|---|---|---|---|---|---|---|---|
| | | | | | | 10 psig (0.069 MPa) in 3 minutes | | | | | | |

$^a$APA = 3-aminophenylacetylene
$^b$As = aminostyrene
$^c$Ns = nitrostyrene

TABLE 3

HYDROGENATION OF 3-NITROPHENYLACETYLENE (NPA)

| Ex. No. | Catalyst paste, wet, grams | NPA, grams Feed | Temp. °C. | Pressure psig H$_2$ (MPa) | Time min. | Pressure drop psig | NPA conc. wt % | NPA conv. wt % | APA$^a$ molar selec. |
|---|---|---|---|---|---|---|---|---|---|
| 23 | Rh$_2$S$_3$, 3.4 | 10 | 100 | 1000 (6.9) | 20 | 120 | 4.8 | 100 | 40$^b$ |
| 24 | Rh$_2$S$_3$, 1.7 | 15 | 100 | 1000 (6.9) | 22 | 70 | 7.0 | 54 | 26$^c$ |
| 25 | ReS$_2$, 1.1 | 10 | 100 | 1000 (6.9) | 72 | 40 | 4.8 | 15$^d$ | 100 |

$^a$APA = 3-aminophenylacetylene
$^b$Product contained 48% aminostyrene
$^c$Product contained 55% nitrostyrene
$^d$Reaction stopped - no further hydrogen uptake Resort may be had to the variations and modifications as fall within the spirit of the invention and the scope of the appended claims.

We claim:

1. A process for the production of an aromatic amino compound containing an acetylene group directly connected to an aromatic ring carbon atom which comprises:

contacting a charge stock comprising an aromatic nitroacetylene compound containing (i) at least one nitro group directly connected to an aromatic ring carbon atom and (ii) at least one acetylenic group having at least two carbon atoms, wherein the acetylene group is directly connected to an aromatic ring carbon atom, and wherein the aromatic portion of said aromatic nitro acetylene compound is selected from the group consisting of benzene, naphthalene, bibenzyl, diphenyl, diphenyl oxide, diphenyl sulfide and benzophenone, in an inert solvent with an unsupported catalyst consisting essentially of ruthenium sulfide and in the added presence of free molecular hydrogen under reaction conditions such that:
   (a) the aromatic nitroacetylene and solvent are maintained substantially in the liquid phase;
   (b) the weight percent of the aromatic nitroacetylene in the inert solvent is from one to about six weight percent;
   (c) the reaction temperature is from 60° C. to 140° C.; and
   (d) the conversion of said nitroaromatic acetylene is greater than 50 weight percent.

2. A process in accordance with claim 1 wherein the charge stock is nitrophenylacetylene.

3. A process in accordance with claim 2 wherein the inert solvent is an organic oxygen containing compound.

4. A process in accordance with claim 3 wherein the organic solvent is selected from the group consisting of alcohols having from 1 to 5 carbon atoms, esters having from 3 to 6 carbon atoms, tetrahydrofuran, p-dioxane, and organic acids having from 2 to 5 carbon atoms.

5. A process in accordance with claim 4 wherein said nitrophenylacetylene is 3-nitrophenylacetylene.

6. A process in accordance with claim 4 wherein the solvent is an alcohol having from 1 to 3 carbon atoms.

7. A process in accordance with claim 6 wherein the solvent is isopropanol.

8. A process in accordance with claim 7 wherein the weight percent of the 3-nitrophenylacetylene in said isopropanol is from 2 to 5.

9. A process in accordance with claim 1 wherein the weight ratio of the nitroaromatic acetylene charge stock to ruthenium as the metal in the catalyst is from 10:1 to 100:1, the weight percent of the nitroaromatic acetylene in the inert solvent is from 2% to 4% and the reaction temperature is from 85° to 125° C.

10. A process in accordance with claim 9 wherein the solvent is an alcohol having from 1 to 3 carbon atoms.

11. A process in accordance with claim 10 wherein the solvent is isopropanol.

12. A process in accordance with claim 13 wherein the nitroaromatic acetylene is a nitrophenylacetylene.

* * * * *